(12) United States Patent
Lampropoulos et al.

(10) Patent No.: US 8,372,021 B2
(45) Date of Patent: Feb. 12, 2013

(54) MEASURING AND TESTING DEVICE FOR RETRACTABLE MEDICAL DEVICES

(75) Inventors: Fred P. Lampropoulos, Salt Lake City, UT (US); Steven R. Taylor, Salt Lake City, UT (US); Thomas D. Stout, Salt Lake City, UT (US); Jim D Mottola, South Jordan, UT (US); Andy E. Poursaid, Sandy, UT (US); Mark Flygare, Farmington, UT (US); Gregory R. McArthur, Sandy, UT (US); Brian Stevens, Pleasant Grove, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 1774 days.

(21) Appl. No.: 11/620,490

(22) Filed: Jan. 5, 2007

(65) Prior Publication Data
US 2008/0167542 A1    Jul. 10, 2008

(51) Int. Cl.
*A61B 5/103* (2006.01)
*A61B 5/117* (2006.01)
(52) U.S. Cl. .................. 600/595; 600/587
(58) Field of Classification Search .......... 604/97.03, 604/100.03; 607/48; 702/45; 600/587
See application file for complete search history.

(56) References Cited

U.S. PATENT DOCUMENTS

| 6,398,777 | B1 | 6/2002 | Navarro et al. |
|---|---|---|---|
| 2004/0116912 | A1 | 6/2004 | Appling |
| 2004/0199151 | A1 | 10/2004 | Neuberger |
| 2006/0085049 | A1* | 4/2006 | Cory et al. .............. 607/48 |
| 2006/0142747 | A1 | 6/2006 | Appling |
| 2006/0200049 | A1* | 9/2006 | Leo et al. ............... 600/587 |
| 2006/0217692 | A1 | 9/2006 | Neuberger |
| 2008/0183163 | A1 | 7/2008 | Lampropoulos et al. |

FOREIGN PATENT DOCUMENTS

| WO | WO 2004/089462 | 10/2004 |
|---|---|---|
| WO | WO 2006/052558 | 5/2006 |

OTHER PUBLICATIONS

O'Reilly et al., "Transcatheter Fiberoptic Laser Coagulation of Blood Vessels," vol. 142, No. 3, Mar. 1992, pp. 777-780.

* cited by examiner

*Primary Examiner* — Melanie Hand
(74) *Attorney, Agent, or Firm* — Stoel Rives LLP

(57) ABSTRACT

This invention relates to a measuring device, which includes a body. A digital display is located in the body, the digital display being configured to show at least a linear measurement. The measuring device also includes a holding portion coupled to the body and configured to slidably engage an elongate member, such as a catheter or introducer sheath, in a space provided between the holding portion and the body. The measuring device also includes a sensor or transducer located in the body and configured to measure at least a linear distance traveled by the elongate member, such that the linear measurement is associated with the linear distance.

25 Claims, 3 Drawing Sheets

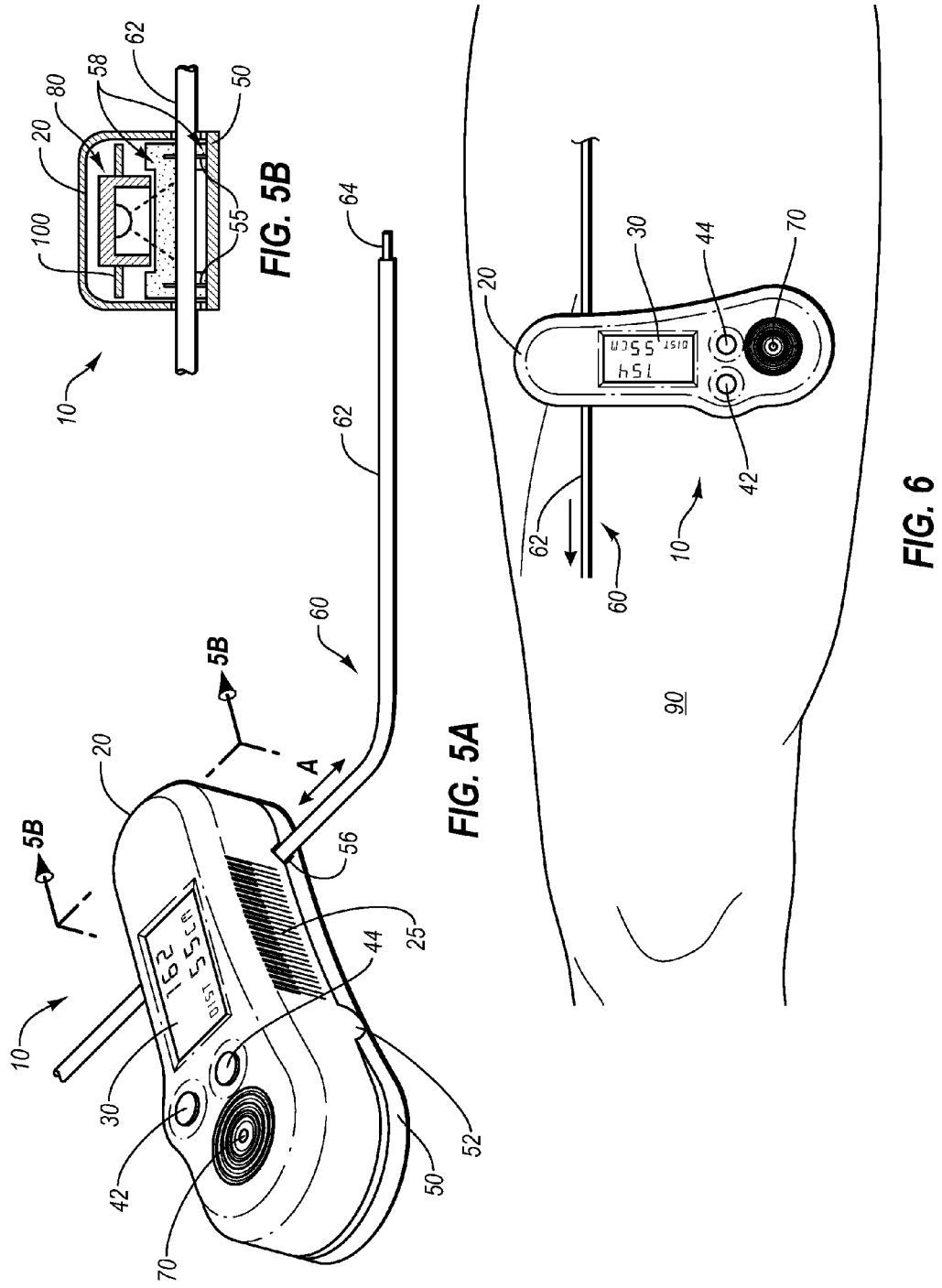

MEASURING AND TESTING DEVICE FOR RETRACTABLE MEDICAL DEVICES

BACKGROUND OF THE INVENTION

The present invention relates to medical treatment devices. In particular, the present invention relates to measuring the distance traveled of a catheter, introducer sheath or other devices. The present invention also concerns related processes, such as measuring the energy of a treatment device, which may include a laser for vein ablation in treating varicose veins, among other things.

Varicose veins exist because valves contained in the walls of the veins fail, allowing blood to stagnate, causing noticeable purple or red traces of the vein visible from the outside of the skin. During a normal vein ablation procedure for varicose veins, a practitioner first identifies a vein or veins for the procedure. The veins are then mapped as a guide for the practitioner in order for him to perform the procedure. Once the veins are mapped, the practitioner prepares the vein for ablation by introducing a sheath into the distal end of the vein, in preparation for introduction of a treatment device, such as a laser or radio frequency device.

The treatment device is introduced into the vein at the distal end and extended in the vein to a junction with a healthy branch of a larger vein to ensure that the entire damaged vein is treated. In a laser treatment procedure, a fiber-optic member is covered by a sheath for introduction and for the treatment procedure. As fiber-optic members are usually very slender fibers of glass, it is not desirable to introduce the fiber-optic member without a covering because the fiber can break off in the patient, or can puncture the vein walls, damaging surrounding tissues.

Thus the fiber-optic member is introduced in a sheath or catheter and advanced to the beginning of the treatment area. The practitioner can determine the location of the tip of the fiber-optic member in the patient by ultrasound imaging, transillumination of the anatomy using an aiming or targeting beam, by feel, and/or by estimating the location based on a calculated position inside of the vein targeted for treatment. Once the fiber-optic member reaches the beginning of the treatment area, the practitioner exposes a portion of the fiber-optic member by extending the fiber-optic member out of the end of the sheath, exposing about 2 cm of fiber, uncovered by the sheath at the treatment end. The laser is then activated and transmits energy through the fiber, thereby heating the tissue and fluid around the end of the treatment fiber, effectively destroying the vein and preventing further filling of the vein with stagnant blood. The ablation procedure removes the appearance of the varicose vein, alleviates the pain caused by the varicose vein and prevents further complications.

In performing the ablation procedure, the practitioner must withdraw the fiber and sheath together at a rate such that neither too much nor too little energy is applied along the vein. To aid the practitioner in determining the withdrawal rate and distance the treatment sheath and fiber remain to be withdrawn, previous treatment sheaths included marks on the sheath body at periodic intervals. By counting the marks, a practitioner could determine how far the sheath had been withdrawn and by subtracting the amount withdrawn from the original inserted length of the sheath, the practitioner could then determine the length of the portion of the sheath remaining inside the patient.

Additionally, in a traditional ablation procedure, a practitioner needs to monitor the energy expended by the laser to ensure sufficient treatment of the target veins. One way to see where the end of the treatment catheter is located inside of the patient is by seeing light through the patient's skin before or during the laser treatment of the target area. Light in the visible spectrum, which may be a targeting light, may be used. Thus, practitioners often dim the lights, allowing better viewing of the monitors and of the treatment location in the patient. A practitioner may also know that an area has been over-treated by patient discomfort and pain.

Thus, in a traditional ablation procedure, a practitioner needs to identify and count markings on the catheter in very low light, simultaneously monitoring the energy output, rate of treatment, location of treatment, and patient comfort.

Some previous efforts to aid the practitioner in managing all of the requirements of the procedure include, for example, a device and method disclosed in U.S. Patent Publication No. US 2006/0217692. In the disclosed device, a system monitors the withdrawal rate and automatically adjusts the energy level of the treatment laser. However, many practitioners do not like the automatic adjustment because the practitioner is consequently limited in her ability to adjust the treatment levels for different or difficult treatment regions. This loss of control forces the practitioner to constantly monitor, second-guess, override, and adjust the machine.

Thus what is needed is a device that aids the practitioner in providing information in an easy-to read and determine format, while still allowing the practitioner control over the procedure.

BRIEF SUMMARY OF AN EMBODIMENT OF THE INVENTION

The present invention relates to medical treatment devices. In particular, according to one embodiment, the present invention relates to a measuring device, which includes a body. A digital display is located in the body, the digital display being configured to show at least a linear measurement. The measuring device also includes a holding portion coupled to the body and configured to slidably engage an elongate member, such as a catheter or introducer sheath, in a space provided between the holding portion and the body. The measuring device also includes a motion sensor located in the body and configured to measure at least a linear distance traveled by the elongate member, such that the linear measurement is associated with the linear distance.

In some embodiments, an energy sensor is included in the measuring device and configured to measure the temperature and/or energy, including a time rate of change of the temperature and/or energy, output at a tip of a treatment member, such as a fiber-optic member. The digital display may be further configured to display an indicator associated with an output of the energy sensor, for example, to indicate that the treatment member is connected to the energy source and working properly, and may include a backlight to allow easy reading in low-light situations. The digital display may be further configured to display units of time, and may be configured to be set to one or more of a plurality of pre-determined distances, based on lengths of the elongate member such that the displayed linear distance is associated with an amount of elongate member extending from the measuring device. Additionally, the digital display may be configured to show at least two different outputs, such as distance and time, or distance traveled by the elongate member and distance remaining of the elongate member extending from the measuring device.

In some embodiments, the motion sensor may be an optical sensor that is configured to detect not only linear motion, but also axial rotation of the tube member. The optical sensor may be located adjacent to the space provided between the holding portion and the body, such that the optical sensor is configured to be adjacent to the elongate member when the elongate member is slidably engaged with the measuring device.

In some embodiments, the holding portion includes a spring member configured to allow the holding portion to pivot between a closed position and an open position. In the closed position, the measuring device can be slidably engaged with the elongate member. And in the open position, the elongate member may be placed into and removed from the measuring device. The spring member may bias the holding portion to the closed position.

Some embodiments include a cushion member located in or substantially adjacent to the space provided between the holding portion and the body, such that the measuring device may accept different sizes of tube members, the cushion member conforming to different diameters of tube members. The cushion member may be further configured to at least partially clean the tube member when the tube member is sliding with respect to the measuring device.

These and other aspects of the present invention will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 5A is a perspective view of the measuring device of FIG. 1, including a tube member slidably engaged with the measuring device;

FIG. 5B is a sectional view of the measuring device of FIG. 5A;

FIG. 6 is a top view of the measuring device of FIG. 1 in use with a patient;

DETAILED DESCRIPTION OF EXEMPLARY EMBODIMENTS

In the illustrated embodiments, aspects and features of a measuring device are disclosed and described below.

Figure 1:
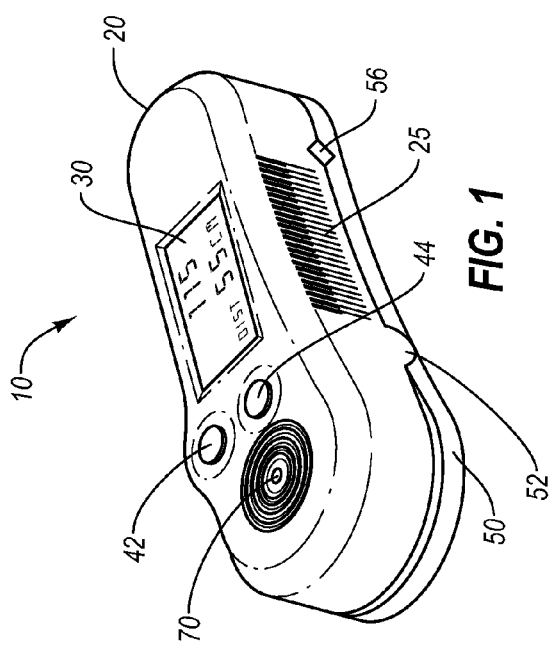
FIG. 1 is a perspective view of an example embodiment of a measuring device.
Figure 2:
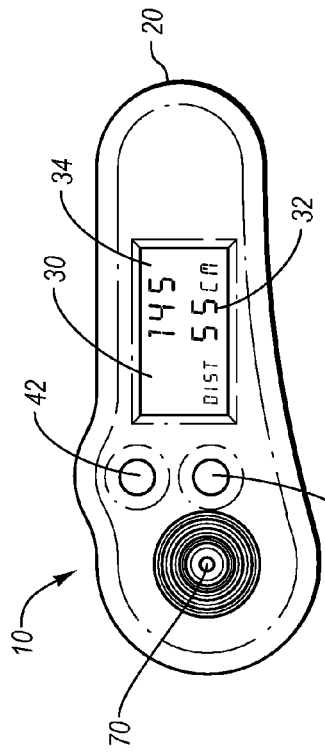
FIG. 2 is a top view of the measuring device of FIG. 1.

FIGS. 1-7 illustrate measuring device 10, including body 20, digital display 30, activation buttons 42, 44, holding portion 50, and operation sensor 70. FIG. 1 shows a measuring device in a configuration for determining the distance traveled of an elongate member, such as tube member 60, for example, as it slides through opening 56.

Figure 8:
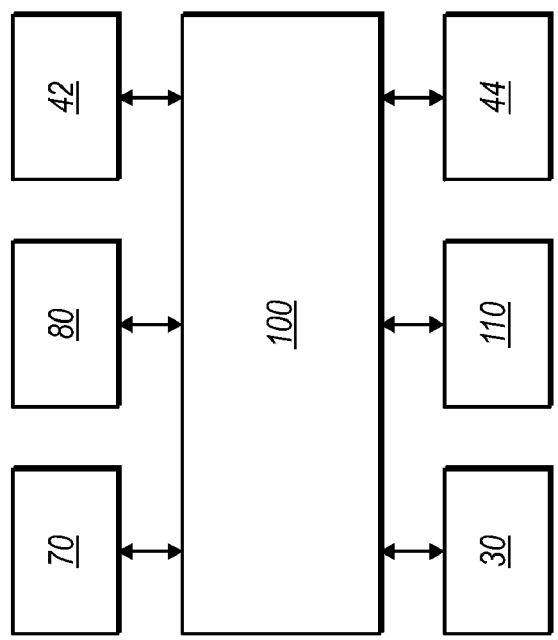
FIG. 8 is a block circuit diagram of an example embodiment of a measuring device.

The body portion 20 may be ergonomically designed, such that a practitioner can easily use measuring device 10. Any ergonomic features may be included in the body 20, such as grip member 25, or a particular shape that would be comfortable or convenient to use. Other ergonomic features may be included that are not specifically shown in the Figures. Body portion 20 may be configured to hold some or all of the necessary operating components inside of body portion 20 for measuring device 10 to perform all functions, such as processors and other circuitry 100, sensor 80, and batteries 110 as shown in FIG. 8.

For example, as shown in all Figures, digital display 30 is included in body 20. Digital display 30 may include two lines of display 32, 34, allowing for different outputs to be displayed simultaneously. For example, digital display 30 may display a measurement output on display line 32, as discussed more fully below, and a timing output on display line 34. Other potential display options are discussed more fully below and may be selected from several desirable display options by those familiar with such devices.

Digital display 30 may include a backlight. A backlight may be configured to be on continuously during use, turned on for a period of time, or turned off, depending on the desired use of measuring device 10. For example, during use in a vein ablation procedure, the procedure is usually performed in low light. The backlight of measuring device 10 may be continuously on during the procedure to allow the practitioner to verify or check position of tube member 60 at a glance. In other embodiments, the backlight may be activated for a period of time by pushing one of activation buttons 42, 44. The period of time may be pre-determined by selecting a desired time, or may be on only when activation button 42 or 44 is pressed. The back lighting function may be pre-programmed into measuring device 10, or may be selectable or programmable by interfacing with measuring device 10.

Measuring device 10 may be configured to measure the distance traveled by an elongate member, such as a tube member 60 shown in FIGS. 5A-7, through opening 56, as discussed below. The elongate member may be a solid member, such as a fiber-optic element without a sheath, a tubular member, such as an introducer sheath containing a fiber-optic element as shown in FIGS. 5A-7, a catheter, guide wire, balloon devices, or any other member that would function with measuring device 10. For purposes of discussion, tube member 60 is shown in the Figures.

Figure 3:
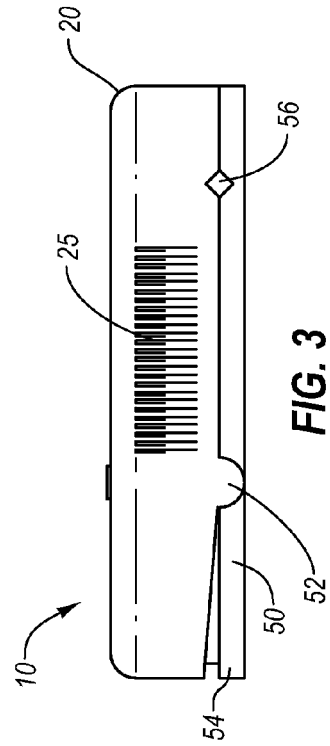
FIG. 3 is a side view of the measuring device of FIG. 1, with the holding portion in a closed position.
Figure 4:
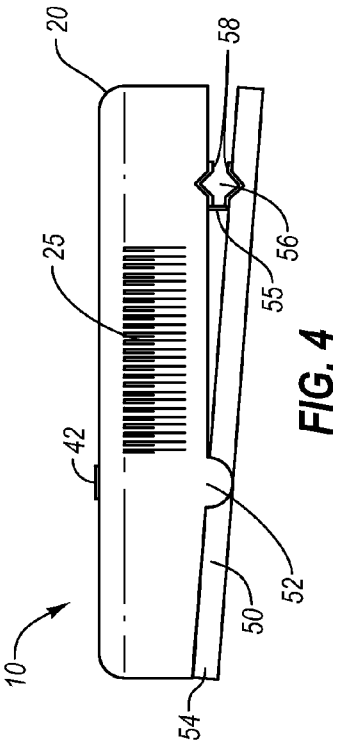
FIG. 4 is a side view of the measuring device of FIG. 1, with the holding portion in an open position.

As shown in FIGS. 3 and 4, measuring device 10 includes holding portion 50 attached to body 20 by hinge 52. A spring member (not shown) is used to bias holding portion 50 in a closed position as shown in FIG. 3, such that the opening 56 is in a closed position. The spring member may be a torsional spring around hinge 52, or may be any other spring member functional to bias holding portion 50 such that opening 56 is in a closed position and allow holding portion 50 to pivot around hinge 52. When end 54 of holding portion 50 is pressed, opening 56 is enlarged and is then in an open position as shown in FIG. 4.

As shown in FIG. 5A, tube member 60 may be placed in opening 56 when holding portion 50 is held to allow opening 56 to be in an open position. Stop portion 55 may limit tube member 60 from entering farther between holding portion 50 and body 20 than opening 56. In effect, stop portion 55 guides tube member 60 into a correct position to be held in opening 56. Stop portion 55 may be one or more protrusions extending from holding portion 50 in to a cavity in body 20, or it may be one or more protrusions from body 20 that extend into complementary portions on holding member 50.

When end 54 is released, holding portion 50 slidably engages tube member 60, such that tube member 60 may slide along axis A without being removed or disengaged from measuring device 10. Opening 56 is shown as including opposing V configurations. While the opening may have a variety of configurations, a V configuration allows a variety of sizes of tube members 60 to be used with measuring device 10. For example, opening 56 may accommodate both 4 and 5 French sizes of tube member 60. Additionally, a V configuration encourages correct positioning of tube member 60 in opening 56, to ensure correct and accurate functioning of measuring device 10.

Pliable cushion 58 is shown in FIG. 4. In FIG. 4, pliable cushion 58 is located on both body 20 and holding portion 50. Pliable cushion 58 may be implemented in a variety of thicknesses and may be made from a variety of materials. For example, pliable cushion 58 may be made from foam material that allows tube member 60 to slide in opening 56, while helping to cushion and support tube member 60. Similarly, pliable cushion may be located on only one side, such as on body 20, and not on holding member 50.

In certain procedures, such as vein ablation, exterior surface 62 of tube member 60 may have blood or other matter on exterior surface 62 of tube member 60 as the member 60 is withdrawn from a patient. Pliable cushion 58 may be made of a material that wipes or cleans tube member 60 as tube member 60 passes through opening 56. Pliable cushion 58 also allows greater variation on sizes of tube member 60 that may be used with measuring device 10. Similarly, pliable cushion 58 also aids in encouraging correct positioning of tube member 60 in cooperation with a V configuration in opening 56.

Although pliable cushion 58 is shown in FIG. 4, measuring device 10 may function without pliable member 58. Similarly, some materials may be used in place of pliable member 58 that may not be pliable, but serve the function of facilitating movement of tube member 60 in opening 56, such as Teflon® or other similar materials.

As shown in FIGS. 5A-5B, tube member 60 may slide in opening 56 along axis A such that tube member 60 does not disengage from measuring device 10. As tube member 60 slides through opening 56, motion sensor 80 cooperates with circuitry (FIG. 8) to measure the movement of tube member 60. Motion sensor 80 may be disposed in body 20 adjacent to opening 56 and, thereby, adjacent to tube member 60 when tube member 60 is engaged in opening 56.

In some embodiments, motion sensor 80 is an optical sensor that detects motion of tube member 60 through opening 56 by reading surface irregularities on tube member 60. Motion sensor 80 may be an LED or a laser diode, such as those used in optical interface devices like an optical computer mouse. Because laser diodes and LEDs may damage eyesight when viewed directly, holding portion 50 is also constructed to shield any harmful light that may be emitted from a laser or LED when used as motion sensor 80.

The motion of tube member 60 passing motion sensor 80 is converted into a distance measurement by circuitry in the measurement device 10. The distance measurement may be displayed on digital display 30. Pliable member 58 may aid in keeping motion sensor 80 free from obstruction by cleaning or wiping tube member 60, as discussed above. Other types of sensors that may be used to measure movement of tube member 60 may include rotary wheels, track balls, ultrasonic sensors, or other sensors appropriate for use in determining velocity or change of position. In some embodiments, a pair or even a plurality of motion sensors may be used.

As discussed above, measuring device 10 may be used to measure and display a distance traveled by a tube member 60, or a length of tube member 60 remaining extending from one end of measuring device 10. In some applications, measuring device 10 is used by selecting, using activation buttons 42, 44, a length, which correlates to a length of tube member 60 to be used in conjunction with measuring device 10. For example, a practitioner may elect to use a tube member 60 for a procedure having a length of 45 cm from the measuring device to a terminal end of tube member 60, which may be inserted into a patient. The practitioner would then select "45 cm" on measuring device 10, and then attach measuring device 10 to the appropriate point on tube member 60 such that movement of tube member 60 resulted in a display on measuring device 10 of the length of the portion of tube member 60 remaining in the patient.

In some embodiments, measuring device 10 may be zeroed when placed into position, such that measuring device 10 displays the amount of distance traveled since the zeroing process, if appropriate for a particular procedure or if preferred by a practitioner. In some embodiments, digital display 30 may display the distance remaining and the distance traveled, each display appearing on one of lines 32 and 34, respectively, as measuring device 10 may be configured to add or subtract distance measurements, depending on the direction of movement and desired display as discussed above.

In other applications, measuring device 10 may include a timing function, which may measure either the elapsed time since starting a timing function on measuring device 10, estimated time remaining for a particular procedure, or both. Different timing functions may be selected using activations buttons 42, 44, as appropriate.

For example, in a vein ablation procedure, as shown in FIG. 6, the practitioner selects and positions tube member 60, such as introducer sheath 62 containing fiber-optic member 64 (see FIG. 5A) for treatment of varicose veins, into the vein of patient 90 to be treated. A distance corresponding to the selected tube member 60 is then selected on measuring device 10 using activation buttons 42, 44. Measuring device 10 is then placed on tube member 60 in the appropriate position on tube member 60. Once measuring device 10 is placed in the appropriate position, activation buttons 42, 44 may be used to select a desired mode, or to begin displaying the desired measurement and/or other desired displays. In some modes, digital display 30 shows a corresponding distance, as selected, which changes as tube member 60 is moved with respect to measuring device 10. In other modes, any combination several values may be displayed, some values may include a rate, such as an average withdrawal rate, a time, such as time remaining or time elapsed, or a distance.

In an ablation procedure, for example, tube member 60 may be withdrawn gradually until the entire vein is treated and the tip of tube member 60 exits patient 90, with digital display 30 indicating, for example, the length of tube member 60 remaining in patient 90 and the time elapsed or alternatively, an average velocity. Measuring device 10 may be held in place on patient 90 manually, by an adhesive, by fasteners, such as a band with hook and loop fabric fasteners, or by any other substances or devices useful to hold measuring device 10 in a location desired by the practitioner.

Figure 7:
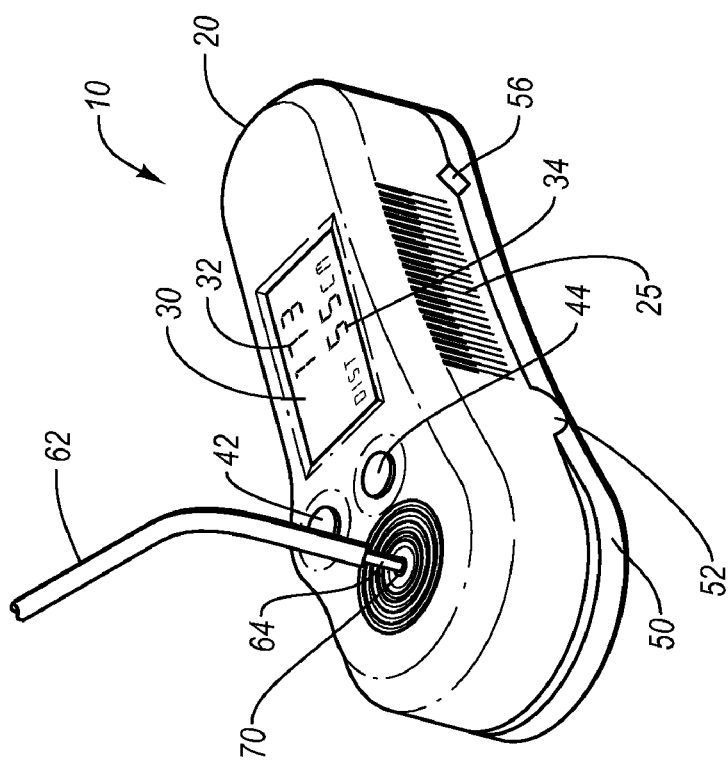
FIG. 7 is a perspective view of the measuring device of FIG. 1, measuring the functionality of a fiber-optic member.

As shown in FIG. 7, measuring device 10 may also be used to test the functionality of fiber-optic member 64, and/or the energy source to which fiber-optic member 64 is connected, prior to use in a procedure. In some instances, the fiber-optic member 64 may be broken internally, or may be disconnected from the energy source at some point unknown to the practitioner prior to performance of the procedure. Since the energy transmitted from a tip of fiber-optic member 64 may be dangerous to vision or touch, a practitioner may want to test the proper functionality of the system, as discussed above, prior to inserting fiber-optic member 64 and introducer sheath 62 into patient 90. For example, in a procedure using a laser, if the laser is not working properly, or if fiber-optic member 64 is broken, time may be wasted in attempting the procedure, equipment may be damaged by energy leaving the system at an undesirable point, or the patient, practitioner, or others may be injured. Some energy sources that may be used with operation sensor 70 may include RF, microwave, ultrasound, heated fluid, radiant light, lasers, electrical conduction, or other energy sources used in medical procedures. The different energy sources may be transmitted along an elongate member made from a material appropriate for the particular type of energy.

FIG. 7 illustrates an embodiment having fiber-optic member 64 in sheath 62, which may be used with a laser in a vein ablation treatment. To test the proper functioning of the laser and fiber-optic member 64 prior to a procedure, a tip of fiber-optic member 64 may be placed in operation sensor 70, located on body 20 of measuring device 10. Operation sensor 70 may be a thermistor configured to sense when a laser, or other energy source, is sending energy through fiber-optic member 64, or through another appropriate medium. Operation sensor 70 may be configured to output a temperature or energy value on digital display 30 corresponding to the temperature or energy of the laser, or digital display 30 may simply indicate that the laser is functioning if the temperature or energy sensed by operation sensor 70 is at a desired threshold. For example, display 30 may warn a practitioner that the power level is too low, not present, or too high.

FIG. 8 illustrates a block circuitry diagram for some embodiments of the invention. As shown, circuitry 100 may be connected to at least activation buttons 42, 44, digital display 30, operational sensor 70, motion sensor 80, and batteries 110. Circuitry 100 may be any processor or circuitry that performs the functions of the measuring devices as described in this application. For example, solid state circuitry, programmable processors, or other devices or circuitry may be used. In some embodiments, additional functional elements may be present as described in this description such as a connection element for connection with an external device, additional sensors, additional digital displays, additional indicators, such as LEDs, or other elements that may be desirable or necessary for the function of measuring device 10.

For example, circuitry 100 may also include a memory (not shown) that can store programs or values to be used by measuring device 10. Circuitry 100 may also be capable of calculating and outputting several values at one time. For example, in some embodiments for use in some medical procedures, a practitioner may encounter a target area of interest that may need to be measured without losing the measurement value for the entire procedure. A target area of interest may include any abnormal tissue in the body, which may be caused by any disease or damage, such as trauma (physical, chemical, electrical), infection, neoplasm, metabolic and autoimmune. Similarly, the area of interest may correspond to a variety of medical procedures, such as vein ablation, placing stents, or other procedures using an elongate member.

In some embodiments, the practitioner may store the current measurement value, rezero, and measure the target area of interest, and then resume the original measurement once the target area of interest is measured. Circuitry 100 may simply store the original measurement or it may simultaneously continue with the original measurement and measure a second measurement starting where the additional measurement is desired. One or both of the original measurement and the additional measurement may be displayed on digital display 30. For example, line 32 may display the original measurement and line 34 may display the additional measurement. Activation buttons 42, 44 may be used to select the desired display and to control the various functions and modes of measuring device 10.

In some embodiments, measuring device 10 may transfer information with an external device, which may be used to monitor or record the progress of the procedure. In some embodiments, the device may be wirelessly connected to the external device or devices. Some external devices may include an energy treatment device, a computer, or other treatment apparatus. In other embodiments, measuring device 10 may stand-alone as a self-contained unit. Similarly, measuring device 10 may include a motor to aid the practitioner in moving tube member 10 at a desirable rate. Measuring device 10 may also calculate a rate of motion by dividing the distance moved by the time elapsed, for example by displaying cm/s. Additionally, a displayed rate may also include time elapsed divided by distance, for example by displaying s/cm.

In some other embodiments motion sensor 80 may detect and display a measurement corresponding to rotational movement of tube member 60 as well as linear movement. For example, some procedures require exact positioning of a specialized tip on an elongate member. Rotational information may be useful in maintaining a desired position of a specialized elongate member or tip when positioned in a patient. Some elongate members that may require rotational precision include guide wires, drainage catheters, bus catheters, balloon catheters, among others.

In some embodiments, holding portion 50 may also be implemented in a door configuration that allows placement of tube member 60 into opening 56 by holding the door open, and then closing and securing the door to slidably engage tube member 60. Similarly, other methods and implements for holding tube member 60 slidably engaged with body 10 may be employed. Such alternatives may include an adhesive fastener, or other suitable mechanism.

It is understood that digital display 30 and activation buttons 42, 44 may be configured in a variety of ways to allow the practitioner maximum comfort and flexibility in using measuring device 10. Similarly, measuring device 10 is not limited to two lines of text on a single digital display 30, or only two activation buttons 42, 44. For example, one single activation button may be sufficient for certain applications. Similarly, three or more buttons may be desirable, along with an additional digital display, such as a video display, in other certain applications. Although vein ablation procedures have been discussed above in connection with embodiments of measuring device 10, it is also understood that embodiments of measuring device 10 may be used in a variety of situations, both during medical procedures and otherwise.

In some embodiments, measuring device 10 may be sterilized for use in medical procedures. Similarly, measuring device 10 may be reusable or disposable. In some embodiments, measuring device may withstand multiple sterilization procedures, or may be configured to be concealed in a sterile sleeve that can be changed as required for sterility.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A measuring device, comprising:
   a body;

a digital display located in the body;
a holding portion coupled to the body and configured to cooperate with the body to define a passageway configured to slidably receive an elongate member;
circuitry located in the body; and
a sensor associated with the circuitry, the sensor located in the body and configured to detect linear motion by the elongate member, wherein the circuitry is configured to determine linear distance associated with the linear motion of the elongate member, and output a signal associated with the linear distance to the digital display;
wherein the holding portion further comprises a spring member configured to allow the holding portion to pivot between a closed position and an open position, the closed position being configured to slidably engage the elongate member, and the open position being configured such that the elongate member may be placed into and removed from the space provided between the holding portion and the body when the holding portion is in the open position, and wherein the spring member biases the holding portion to the closed position.

2. The measuring device of claim 1, wherein the elongate member comprises an energy conducting member, and wherein:
the sensor is a first sensor; and
wherein the measuring device further comprises a second sensor configured to measure energy at a terminal end of the energy conducting member.

3. The measuring device of claim 2, wherein the digital display is further configured to display an indicator associated with an output of the second sensor.

4. The measuring device of claim 2, wherein the energy conducting member is a fiber-optic member, and wherein the energy is light energy generated by a laser.

5. The measuring device of claim 1, wherein the sensor is an optical sensor.

6. The measuring device of claim 5, wherein the sensor is further configured to detect axial rotation of the elongate member.

7. The measuring device of claim 5, wherein the optical sensor is located adjacent to the passageway, such that the optical sensor is configured to be proximate to the elongate member when the elongate member is slidably engaged with the measuring device.

8. The measuring device of claim 1, wherein the elongate member is selected from one of a catheter, and an introducer sheath.

9. The measuring device of claim 1, wherein the elongate member is a fiber-optic member contained within a tube member.

10. The measuring device of claim 9, wherein the fiber-optic member is configured to treat blood veins with light energy.

11. The measuring device of claim 1, wherein the digital display includes a backlight.

12. The measuring device of claim 1, wherein the digital display is further configured to display units of time.

13. The measuring device of claim 1, wherein the digital display is further configured to be set to display one or more of a plurality of pre-determined distances, wherein the pre-determined distances are associated with lengths of the elongate member such that the linear distance is associated with an amount of elongate member extending from the measuring device.

14. The measuring device of claim 1, wherein the digital display is configured to show at least two different outputs, wherein a first output is associated with the linear distance.

15. The measuring device of claim 1, wherein the measuring device is configured to communicate with a device remote from the body.

16. The measuring device of claim 15, wherein the device remote from the body is a laser treatment device.

17. The measuring device of claim 15, wherein the device remote from the body is a computer.

18. The measuring device of claim 1, further comprising a cushion proximate the passageway, the cushion being configured such that the measuring device may accept different sizes of elongate members.

19. The measuring device of claim 18, wherein the cushion is further configured to at least partially clean an outside surface of the elongate member when the elongate member is sliding with respect to the measuring device.

20. A device for use in a medical procedure, comprising:
a body;
a motion sensor located in the body, the motion sensor being configured to sense motion of an elongate member moving with respect to the motion sensor, and wherein the motion sensor is configured to output a signal associated with the motion of the elongate member;
circuitry located in the body and coupled to the motion sensor, the circuitry being configured to output a value associated with the signal;
a digital display located in the body and coupled to the circuitry, the digital display being configured to display the value associated with the signal; and
a holding portion comprising a spring member configured to allow the holding portion to pivot between a closed position and an open position, the closed position being configured to slidably engage the elongate member, and the open position being configured such that the elongate member may be placed into and removed from the space provided between the holding portion and the body when the holding portion is in the open position, and wherein the spring member biases the holding portion to the closed position.

21. The device of claim 20, wherein the circuitry includes a timer, and wherein the value associated with the signal is a rate having the units of s/cm.

22. The device of claim 20, wherein the circuitry includes a timer, and wherein the value associated with the signal is a rate having the units of cm/s.

23. The device of claim 20, wherein the digital display includes a backlight.

24. The device of claim 20, wherein the circuitry includes a memory configured to store a plurality of lengths.

25. The device of claim 24, wherein the value is a first value,
wherein the circuitry is configured to output a second value,
wherein the digital display is configured to selectively display the first value or the second value or both values simultaneously, and
wherein the memory is further configured to store the first value when the second value is being displayed and the first value is not being displayed.

* * * * *